Figure 1:
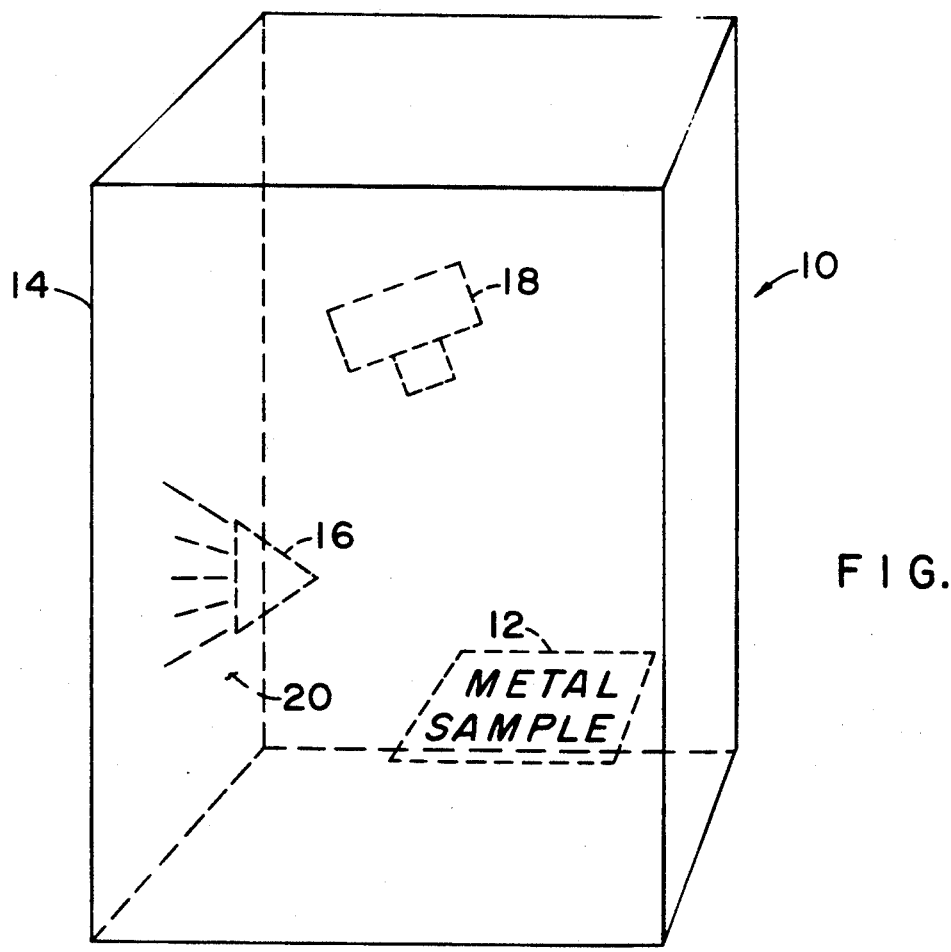

United States Patent [19]

Chang

[11] Patent Number: 5,146,311
[45] Date of Patent: Sep. 8, 1992

[54] METHOD OF INDENTIFYING AND QUANTIFYING OXIDES ON ROLLED METAL STRIP

[75] Inventor: Robert C. Chang, Export, Pa.

[73] Assignee: Aluminum Company of America, Pittsburgh, Pa.

[21] Appl. No.: 718,434

[22] Filed: Jun. 21, 1991

[51] Int. Cl.$^5$ .............................................. H04N 7/18
[52] U.S. Cl. ...................................... 358/100; 358/101
[58] Field of Search ............... 358/100, 101, 106, 107; 382/8

[56] References Cited

U.S. PATENT DOCUMENTS 4,319,270  3/1982  Kimura et al. ................... 358/100 X
4,561,104  12/1985  Martin ............................. 358/100 X Primary Examiner—Victor R. Kostak
Attorney, Agent, or Firm—Elroy Strickland

[57] ABSTRACT

A method of determining the severity of oxides rolled onto the surfaces of metal strips subjected to rolling operations. The method includes identifying different types of rolled-on oxides, and comprises providing image pixels of at least a portion of a strip surface that contains oxides. The image pixels are filtered to identify oxides extending in a fixed direction and are thresholded to segment oxides from other surface features extending in the fixed direction. All pixel ares and/or intensities that are above a threshold value employed in the thresholding step are summed to obtain the total amount of oxides on the strip surface.

7 Claims, 4 Drawing Sheets

METHOD OF INDENTIFYING AND QUANTIFYING OXIDES ON ROLLED METAL STRIP

BACKGROUND OF THE INVENTION

The present invention is directed generally to the problem of oxides rolled onto the surfaces of metal strips in a rolling mill, and particularly to identifying and quantifying rolled-on oxides from video images of surfaces containing oxides.

Oxide residues sometimes occur on the bare metal surfaces of hot rolled and cold rolled aluminum alloys. The formation of such residues is not completely understood and, as a consequence, the elimination of such oxides has not been totally effected. For aesthetic reasons it is preferred that the surfaces of bare metal not contain any substantial amount of oxides.

Since the elimination of oxides has not been effected in rolling processes, the severities of the oxides must be evaluated so that steps can be taken to at least attempt an alleviation of the problem.

Current evaluation practices require visual inspection by trained quality assurance personnel. Such personnel visually examine small pieces of metal samples that have been removed from a wrap or wraps of large coils of the metal, and assign grades to the oxide residues. The grades represent respective oxide severities.

The human eye has limited resolution and sensitivity so that the scoring or grading process provides finite, discrete grade levels, as opposed to a continuous or infinite number (at least theoretically) of grade levels.

In addition, the task of visually inspecting metal samples is laborious, and the consistency and accuracy of the grading process is not always reliable.

BRIEF SUMMARY OF THE INVENTION

The present invention is directed to an electronic imaging technique that provides automatic measurement and grading of oxide residues. The technique involves generally the acquisition of a digital image of a metal surface, and processing the image to 1) identify oxides and quantify the total amount of oxides in the acquired image, 2) for hot rolled metals, identify oxide types (streaks, specks, and background oxides), and 3) quantify the amounts of oxides in each oxide type. Generally, oxide residues occur in the hot rolling process, as opposed to cold rolling.

An objective of the invention is therefore to provide automated means to classify oxide types and quantify the amounts of each type.

Another objective of the invention is to provide repeatably consistent and accurate oxide inspection results so that the rolling process that produces the oxides can be controlled to reduce oxide formation.

Yet another object of the invention is to improve resolution of oxide measurements, which includes continuous oxide severity values, as opposed to the discreet levels provided by visual inspection. Automation of the identification and quantification processes also reduces inspection costs.

THE DRAWINGS

The invention, along with its objectives and advantages, will be better understood from consideration of the following detailed description and accompanying drawings in which:

FIG. 1 is a schematic representation of apparatus adapted to acquire images of metal surfaces containing oxides.

Figure 2:
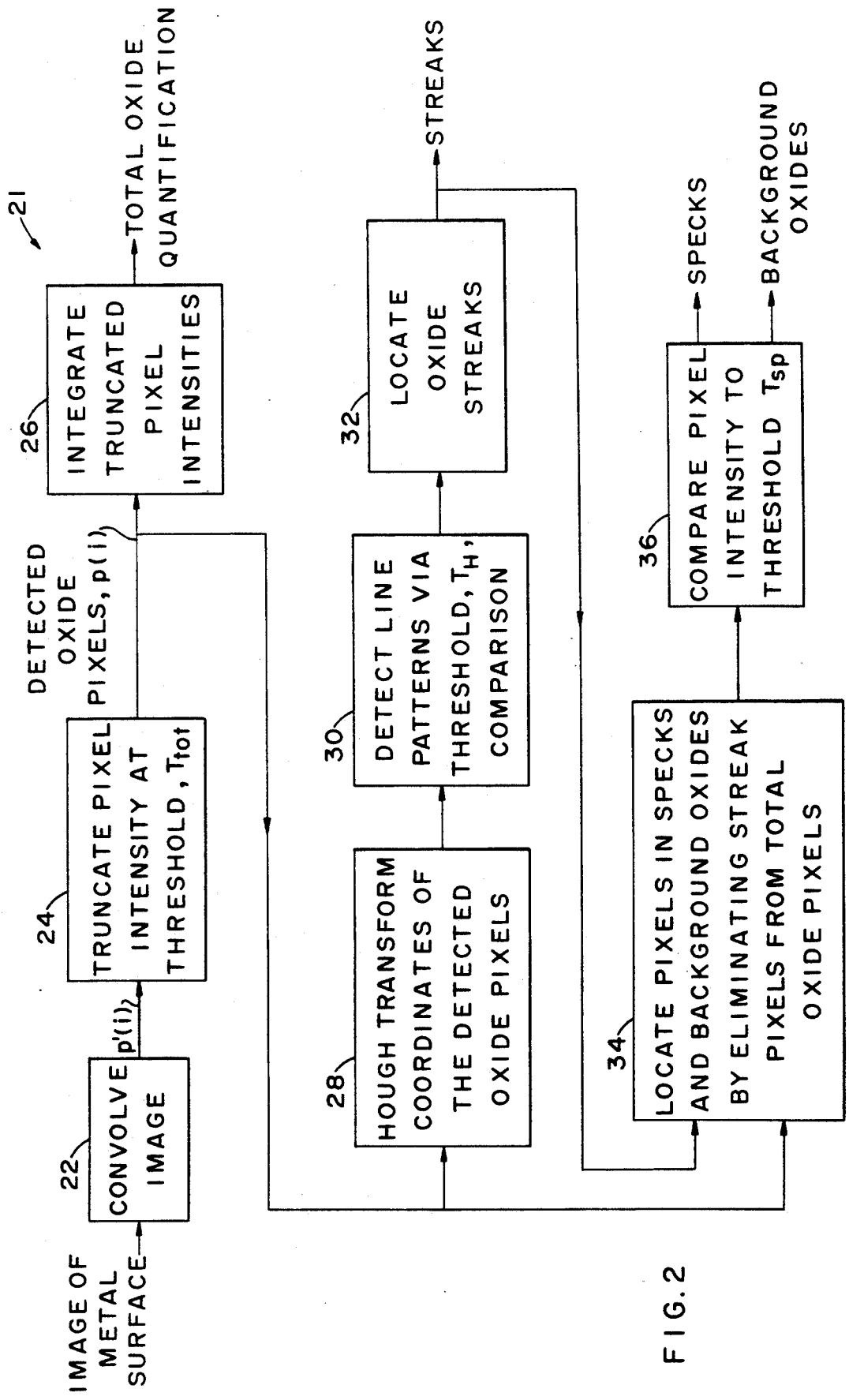
Figure 3:
Figure 4:
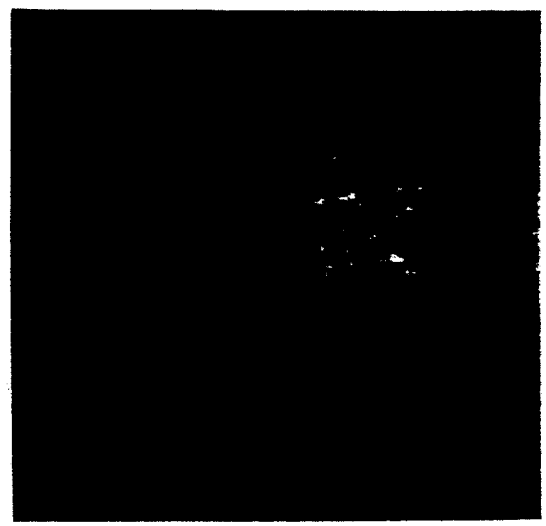
Figure 5:
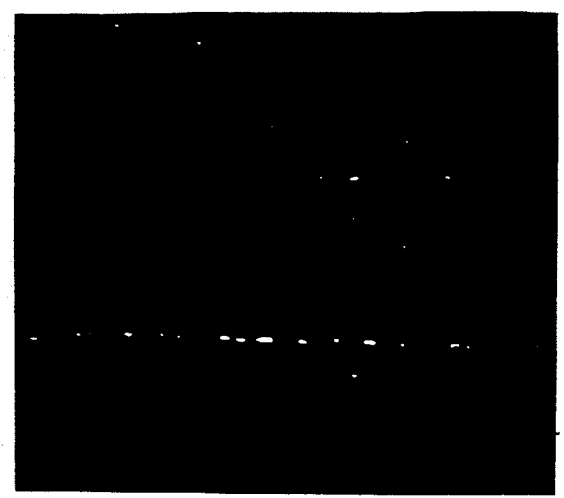
Figure 6:
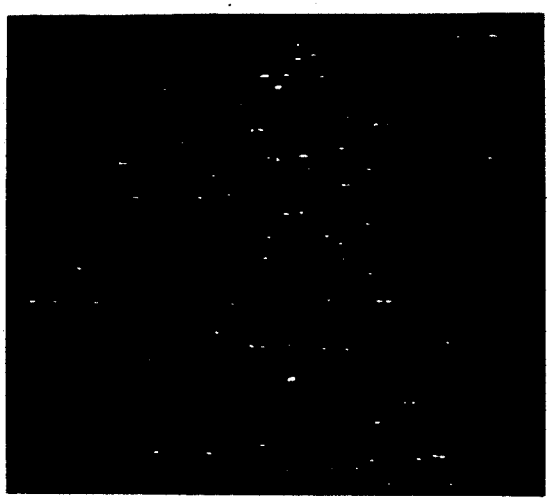
Figure 7:
Figure 8:

FIG. 2 is a block diagram showing the paths of data flow in processing the images acquired in FIG. 1, FIG. 3 is an image of an aluminum surface containing streak and background oxides, as provided by a CRT screen, the screen having been photographed to provide a glossy picture of the image, FIG. 4 is an image of a metal surface containing specks and background oxides provided by the means of FIG. 1, FIGS. 5 and 6 show detected oxides after convolution and thresholding of the images of FIGS. 3 and 4, FIG. 7 shows the location of the detected oxide streak of FIG. 3 in the image acquired by the means of FIG. 1, and FIG. 8 is a photograph showing the locations of the specks of FIG. 4 minus the background oxides.

PREFERRED EMBODIMENT

Referring now to FIG. 1 of the drawings, an apparatus 10 is schematically shown that provides a controlled illumination environment for obtaining consistent video images of the surface of a metal sample 12. The sample can be taken from a large coil of metal (not shown) suspected of containing oxide residues.

Specifically, the apparatus comprises a cabinet 14 that completely encloses a light source 16, a television camera 18 and metal sample 12. The inside wall surfaces of cabinet 14 are reflective in a manner that illuminates the surface of the metal sample with a soft, uniform intensity of visible light radiation.

Camera 18 acquires an image of the surface of 12, and produces an output in the form of picture pixels; the pixels are electrical (digital) subdivisions of the image provided by a light sensitive, solid state matrix of the camera.

A light source that has proven effective for properly illuminating an aluminum sample 12 is a Smith-Victor, model 770 quartz-light unit, though other light sources can be used. As shown in FIG. 1, the output of the source is directed at a wall surface 20 of enclosure 10, surface 20 reflecting light to the other surfaces of the enclosure and to the surface of sample 12. All surfaces of enclosure 14 reflect light to sample 12 in a manner that illuminates the surface of 12 to be examined in a generally uniform manner. In addition, the light is a soft, non-glaring light so that all features on the sample surface will be substantially evenly illuminated.

Camera 18 can be a Cohu 6414-15CCD (charged coupled, solid state matrix) camera provided with a JML 12.5-75 mm zoom lens. Other viewing equipment, however, can be used to acquire surface images.

The location of sample 12 in relation to camera 18 and light source 16, and the reflecting walls of the cabinet is optimized for imaging oxides that are contained on an otherwise bare surface background of a metal strip or sheet, i.e., the surface of sample 12 exposed to light and to the lens of camera 18 is positioned in a way that oxides on the surface have substantially darker or lower intensities or shades than the background of the bare metal of the sample. In addition, the sample is oriented in such a way that the rolling direction of the sample is at a fixed direction, which is horizontal in the digitized image. Any roll marks and roll grind lines that might be formed on the sample surface are so small that in the digitized image they are extremely light so as to be unnoticable. In this manner, camera 18 and a convolution filter 22 (FIG. 2) will be able to discern oxide streaks, as well as provide an output that contains the total amount of all oxides and individually the amounts of streaks, specks and background oxides in a manner presently to be discussed.

Oxides are small, slightly dark particles that become elongated in the direction at which a strip is rolled. Specks are sparsely distributed particles and considerably darker than the elongated oxides. Streaks are concentrations of oxide particles that form line patterns in the rolling direction. All other oxides are grouped together and are considered as background.

FIG. 3 of the drawings is a computer processed image (which has been photographed) containing background oxides and an oxide streak, while FIG. 4 is an image showing a measurement of oxide specks and background oxides, both figures being pictures of surface portions of a hot-rolled anodized sheet of 3004 aluminum alloy.

The pixel output of camera 18 is sent to an image analyzer 21, which comprises the elements of and performs the functions depicted in FIG. 2 of the drawings. The analyzer provides a digital version of the image of the surface under examination. Component parts of the image, i.e., pixels, are directed to means 22 of analyzer 21 in digital form for convolving pixel data. Means 22 is preferably a convolution filter, such a filter having horizontal and vertical constants that are effective in detecting oxide particles that have been elongated in the direction at which the strip was rolled. (In the process of reducing the gauge of a strip in a rolling mill, the force of the rolls of the mill against the strip elongates oxide particles that are on the surface of the strip). These elongated particles are physically (visually) different from background oxidation and from oxides specks. An edge-detecting filter can sense items and marks on a surface that extend in one direction. The edge of the sample 12 are not detected, as the image provided by the camera is wholly within the boundaries of the sample.

The convolution filter 22 can be part of a signal processing (computing) workstation (shown only functionally in FIG. 2) that includes the remainder of the processes of the invention presently to be described. Any workstation or system hardware can be used to analyze the image, as long as the image is digitized. Software is written for the system, the software containing the algorithm of the present invention. The convolution effected by filter 22 removes the dc (average) component of pixel intensities and enhances elongated features for subsequent line pattern detection. For example placing a metal sample such that the rolling directing is horizontal in the digital image, the image can be convolved with the following 3×3 filter:

$$\begin{bmatrix} -1 & -1 & -1 \\ +1 & -2 & +1 \\ +1 & +1 & +1 \end{bmatrix} \quad (1)$$

This matrix of the filter employs mathematical (adding and multiplying) operations to obtain filtered values of image pixels. These values determine the existence of horizontally elongated features in the image.

After the convolution, the high intensity contrast of oxides with the background of bare metal, as discussed earlier, allows the oxides seen by camera 18 to be segregated from other surface features (roll grind patterns etc) of sample 12 by applying at 24 a threshold value $T_{tot}$ to the convoluted image provided by filter 22 such that all pixels having intensities greater than the threshold $T_{tot}$ are considered oxides.

The total amount of oxides on the surface of 12 in terms of both size (area) and shades (intensities) are computed at 26 as the summation of all oxide intensities detected by the thresholding process of 24. Specifically, total oxides in said image = $\Sigma p(i)$ where p(i)s are pixel intensities after thresholding, specifically, where $p(i) = p'(i) - T_{tot}$ for all $p'(i) > T_{tot}$, $P(i) = 0$ for all $p'(i) \leq T_{tot}$, and $\quad (2)$ p'(i) are pixel intensities in the filtered image but before thresholding.

The oxide pixels detected and therefore made available by thresholding are further processed, i.e., integrated, at 26. Such integration provides a value representing the total severity of the oxides found on the surface of sample 12 exposed to camera 18.

FIGS. 5 and 6 show the oxides detected by thresholding that are seen originally in the images of FIGS. 3 and 4. Since only those pixels having intensities above the threshold of 24 are made available for further processing, the computation at 24 is also a "truncating" process.

Elongated oxide streaks are recognized by identifying possible line patterns in the image extending in the rolling direction after the thresholding step. For this purpose a Hough transformation (box 28) is applied to the x-y coordinates of the detected oxide pixels and is run at the above workstation and system. The transformation hence identifies streaks by first applying a morphological operation (the Hough transformation) to the coordinates of all detected oxide pixels, which is then followed by applying a threshold value TH (box 30) to the results of the morphological operation. The thresholding at 30 establishes a streak filter, the filter being effective to locate oxide streaks in the image, as seen in FIG. 7 and as indicated functionally by box 32 in FIG. 2.

An increased number of total detected oxide pixels will cause exponentially increased computation in the morphological process, but offers the opportunity to detect even the lightest streaks when a proper value is chosen for $T_H$. However, increasing the numbers oxide pixels increases the probability of having oxides falsely forming a line or streak pattern.

Oxide streaks 32 can be quantified by integrating the intensities of the oxide pixels within the streaks detected by using the equation:

oxide streaks = $\Sigma p(j)$ $\quad (3)$ where p(j) represents filtered and truncated pixel intensities of the streaks detected at 28; such streaks, of course, are a part of the total oxides provided at 26.

The algorithm of the invention includes further identification and quantification of oxide specks and background oxides. As shown in FIG. 2, the oxide streak value 32 is brought together at 34 with the totality of oxides provided by the thresholding process of 24 so that the algorithm can now operate to disregard the streak value and thereby eliminate the same from the totality of oxides. The remaining value will be oxide specks and background oxides.

A third thresholding process is now employed at 36, where the substantially darker specks and lighter background are compared to a threshold value Tsp. The comparison process can be expressed mathematically as follows:

$$\text{oxide specks} = \Sigma p(k) \text{ for all } p(k)s > Tsp \quad (4)$$

$$\text{background oxides} = \Sigma p(k) \text{ for all } p(k)s < Tsp \quad (5)$$

where p(k)s are filtered and truncated intensities of oxide pixels excluding those belonging to detected streaks 32, and Tsp is the threshold value applied to the intensities of oxide pixels after being filtered at 22 and truncated by threshold $T_{tot}$ at 24.

FIG. 8 is a computer print of specks only i.e., without the other oxides being visible, and the locations of the specks within the image provided by camera 18.

With removal of both streak and speck oxides, background oxides remain, and are identified as such by the comparison process of 36. And, specks and background oxides are of such a nature (i.e., difference in darkness or pixel intensities) that thresholding alone provides their detection.

The specks and background oxides can be separately quantified by intensity integration in the manner described above in quantifying total oxides.

The quantification of oxides in the present invention involves integration of the oxide intensities reaching camera 18. The computations involved are implicitly affected by both the area of the oxides as well as their intensities or shades. The quantifications of the three types of oxides can be combined to provided another method of reaching total oxide quantity, i.e., another method besides that provided at 26.

In the algorithm and processes of the invention the three oxide types can be mutually exclusive, where streaks do not contain specks and background oxides, etc. However, the processing algorithm of the invention can be adjusted for non-mutual exclusive criteria, as discussed above in connection with threshold $T_H$ and as shown in FIGS. 3 and 4, for example. Similarly, $T_{tot}$ and Tsp are settable within a wide range of values to achieve proper and correct ranking of the severities of specks and background oxides. Such thresholding allows a theoretically infinite amount of gradings, as shade and distribution are continuous variables in the mathematics of the computations. When quality personnel visually inspect metal sheet or samples of sheet, they assign discrete scores or grades for oxide content falling within arbitrary ranges of the scores. Hence, the processes of the invention provide a better grading system since all shades or intensities of oxides can be made available for quality control. The machine vision of the system hence provides better resolution than the human eye, and is repeatably consistant.

While the invention has been described in terms of preferred embodiments, the claims appended hereto are intended to encompass all embodiments which fall within the spirit of the invention.

What is claimed is:

1. A method of determining the severity of oxide formations on a rolled metal strip, comprising:

illuminating said strip with light, acquiring and digitizing an image of a surface of the strip in a manner that orients oxides in a fixed direction and contrasts the oxides in the acquired image with the background of the bare metal of the strip, as it is appears in the acquired image, removing the average value of pixel intensities of the images to provide a filtered image of the strip surface, thereby enhancing elongated features in the image that represent surface oxides, identifying oxides in the pixels of the filtered image having intensities above a predetermined threshold, and quantifying the amount of such identified oxides by summing the intensities of their pixels.

2. The method of claim 1 including performing a filtering step with an edge-detection convolution filter.

3. The method of claim 1 including
    identifying oxide streaks in the image by applying a Hough transformation to the coordinates of the oxide pixels.

4. The method of claim 3 in which transform values are provided by the Hough transformation, the method including
    comparing said values to a threshold value $T_H$, the threshold value establishing an oxide streak filter that locates oxide streaks in the image.

5. The method of claim 3 including the steps of quantifying the intensities of the streaks by integrating the filtered intensities of the oxide pixels located within the areas of the streaks, using the equation $$\text{oxide streaks} = \Sigma p(j)$$

where p(j) represents pixel intensities of oxide streaks after filtering and thresholding that are part of the total rolled-in oxides.

6. The method of claim 3 in which oxide specks and background oxides are separated from each other and from oxide streaks by threshold comparison of the specks and background by use of the following equations:

$$\text{oxide specks} = \Sigma p(k) \text{ for all } p(k) > T_{sp}, \text{ and}$$

$$\text{background oxides} = \Sigma p(k) \text{ for all } < T_{sp}$$

where the p(k)'s are intensities of the oxide pixels after filtering and thresholding that exclude those of the detected streaks, and $T_{sp}$ is the threshold applied to filtered intensities of all remaining oxide pixels.

7. A method of determining the severity of oxides rolled onto the surfaces of metal strips subjected to rolling operations, the method comprising:

arranging a video camera and illumination to acquire and digitize images of a surface of a metal strip in a manner that contrasts the oxides in the acquired images with the background of the bare metal of the strip surface, locating said surface in a manner that orients oxides in a fixed direction for image acquisition by the camera, filtering pixel intensities of said image by use of an edge-detection convolution filter that (1) removes the average value of the intensities from the image and (2) enhances elongated features in the image that are oxides, identifying oxides in the filtered image as pixels having intensities above a threshold value $T_{tot}$, and quantifying the severity of such identified oxides in terms of the total amount of oxides by summing the intensities of the pixels subjected to filtering and thresholding using the equation total oxides in said image $= \Sigma p(i)$ where the p(i) are pixel intensities after thresholding, specifically, where $p(i) = p'(i) - T_{tot}$ for all $p'(i) > T_{tot}$, $P(i) = 0$ for all $p'(i) \leq T_{tot}$, and p'(i) are pixel intensities in the filtered image but before thresholding.

* * * * *